(12) United States Patent
Steinmann et al.

(10) Patent No.: US 6,316,552 B1
(45) Date of Patent: Nov. 13, 2001

(54) DIACRYLATES AND DIMETHACRYLATES

(75) Inventors: Bettina Steinmann, Praroman; Adrian Schulthess, Tentlingen; Max Hunziker, Düdingen, all of (CH)

(73) Assignee: Vantico Inc., Los Angeles, CA (US)

( * ) Notice: Subject to any disclaimer, the term of this patent is extended or adjusted under 35 U.S.C. 154(b) by 0 days.

(21) Appl. No.: 09/483,057

(22) Filed: Jan. 13, 2000

Related U.S. Application Data

(62) Division of application No. 08/342,955, filed on Nov. 21, 1994, now Pat. No. 6,043,323, which is a continuation of application No. 08/006,444, filed on Jan. 21, 1993, now abandoned.

(30) Foreign Application Priority Data

Jan. 27, 1992 (CH) .................................................. 216/92

(51) Int. Cl.$^7$ ............................ C08G 59/16; C08F 283/10
(52) U.S. Cl. ........................ 525/531; 525/529; 525/530; 525/922
(58) Field of Search .................................. 525/529, 530, 525/531, 922

(56) References Cited

U.S. PATENT DOCUMENTS 4,056,453   11/1977   Barzynski et al. .................... 428/425

(List continued on next page.)

FOREIGN PATENT DOCUMENTS 3446910   7/1985   (DE) .

(List continued on next page.)

OTHER PUBLICATIONS

Derwent Abstr. 92–3258840/40 for EP 506616.

(List continued on next page.)

*Primary Examiner*—Robert Dawson
*Assistant Examiner*—Jeffrey B. Robertson
(74) *Attorney, Agent, or Firm*—Lyon & Lyon LLP

(57) ABSTRACT

Compounds of formulae (Ia) and (Ib)

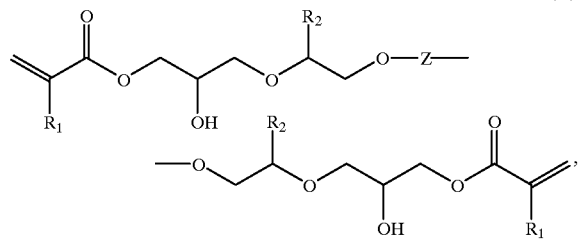

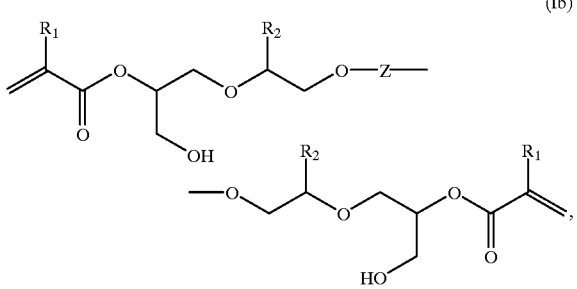

wherein the substituents $R_1$ are each independently of the other hydrogen or methyl, $R_2$ is an unsubstituted $C_1$–$C_{20}$alkyl group or a $C_1$–$C_{20}$alkyl group which is substituted by one or more than one substituent selected from the group consisting of hydroxy, $C_6$–$C_{14}$aryl and halogen, an unsubstituted phenyl group or a phenyl group which is substituted by one or more than one substituent selected from the group consisting of $C_1$–$C_6$alkyl, hydroxy or halogen, or is a radical of formula —CH$_2$—OR$_3$, wherein $R_3$ is an unsubstituted $C_1$–$C_{20}$alkyl group or a $C_1$–$C_{20}$alkyl group which is substituted by one or more than one substituent selected from the group consisting of hydroxy, $C_6$–$C_{14}$aryl and halogen, an unsubstituted phenyl group or a phenyl group which is substituted by one or more than one substituent selected from the group consisting of $C_1$–$C_6$alkyl, hydroxy and halogen, or is a $C_2$–$C_6$alkenyl group, a $C_2$–$C_{20}$acyl group or an unsubstituted cyclohexylcarbonyl group or a cyclohexylcarbonyl group which is substituted by one or more than one substituent selected from the group consisting of $C_1$–$C_6$alkyl, hydroxy and halogen, Z is a group of formulae (IIa)–(IIe)

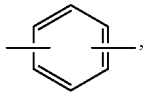

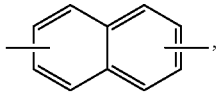

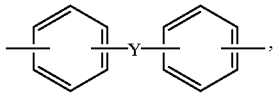

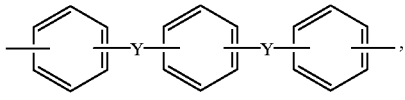

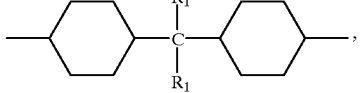

wherein Y is a direct bond, $C_1$–$C_6$alkylene, —S—, —O—, —SO—, —SO$_2$— or —CO—, and $R_1$ is hydrogen or methyl, and wherein the aromatic and cycloaliphatic rings of formulae (IIa)–(IIe) are unsubstituted or substituted by one or more than one substituent selected from the group consisting of $C_1$–$C_6$alkyl, chloro and bromo, form, in conjunction with other acrylates or methacrylates, low viscosity photocurable compositions which, when fully cured, give moulded articles of excellent flexibility.

7 Claims, No Drawings

U.S. PATENT DOCUMENTS

| | | | |
|---|---|---|---|
| 4,097,994 | 7/1978 | Reaville et al. | 525/531 |
| 4,169,732 | 10/1979 | Shipley | 96/35.1 |
| 4,284,574 | 8/1981 | Bagga | 260/348.43 |
| 4,575,330 | 3/1986 | Hall | 425/174.4 |
| 4,836,832 | 6/1989 | Tumey et al. | 427/44 |
| 5,015,701 | 5/1991 | Domeier | 525/922 |
| 5,084,353 | 1/1992 | Cobbledick et al. | 428/413 |
| 5,180,757 | 1/1993 | Lucey | 522/76 |
| 5,215,863 | 6/1993 | Nawata et al. | 522/102 |
| 5,229,252 | 7/1993 | Flynn et al. | 522/101 |

FOREIGN PATENT DOCUMENTS

| | | |
|---|---|---|
| 0022073 | 11/1980 | (EP) . |
| 0292219 | 11/1988 | (EP) . |
| 0378144 | 2/1991 | (EP) . |
| 0425441 | 5/1991 | (EP) . |
| 60-118710 | 6/1985 | (JP) . |
| 02-265477 | 10/1990 | (JP) . |

OTHER PUBLICATIONS

Chemical Abstr. 103:150986k.

Chemical Abstr. 116:49053x.

Derwent Abstr. 91–126891/18.

DIACRYLATES AND DIMETHACRYLATES

This is a divisional of application Ser. No. 08/342,955, now U.S. Pat. No. 6,043,323, filed on Nov. 21, 1994, which is a continuation of Ser. No. 08/006,444 filed Jan. 21, 1993, abandoned.

The present invention relates to novel acrylates and methacrylates, to photosensitive compositions containing these compounds and to a process for the preparation of three-dimensional objects from said photosensitive compositions.

Radiation-sensitive liquid resins or resin systems can be used for a variety of utilities, typically as coating compositions, adhesives or photoresists. Quite generally, liquid resins or resin systems should also be suitable for fabricating three-dimensional objects by the stereolithographic technique described in U.S. Pat. No. 4,575,330; but many resins prove to be too viscous, whereas others are insufficiently light sensitive or suffer too severe shrinkage during the cure. The strength properties of the moulded articles or objects made from photocured resins are also often unsatisfactory.

Liquid resin systems for stereolithography comprising different mono- and diacrylates and mono- and dimethacrylates as well as a urethane acrylate or methacrylate and a monomeric or oligomeric diacrylate or methacrylate derived from bisphenol A or bisphenol F are disclosed in EP-A 425 441. When precured with laser light, these systems give green stages of superior green strength and, after the full cure, rigid-elastic objects whose flexibility is, however, insufficient for certain utilities.

EP-A 506 616 discloses liquid resin compositions of several acrylates and/or methacrylates which contain further hydroxyl group containing aliphatic or cycloaliphatic acrylates and/or methacrylates. The cured moulded articles made from these compositions by stereolithography have superior flexibility and tear propagation strength. A drawback of these compositions for processing in mechanical apparatus, however, is their rather high viscosity.

It has now been found possible to prepare novel hydroxyl group containing acrylates and methacrylates which, in conjunction with other acrylates or methacrylates, form low viscosity photocurable compositions which, when fully cured, give moulded articles of excellent flexibility.

Accordingly, the invention relates to compounds of formulae (Ia) and (Ib)

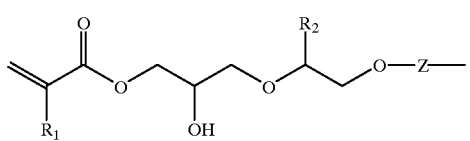

(Ia)

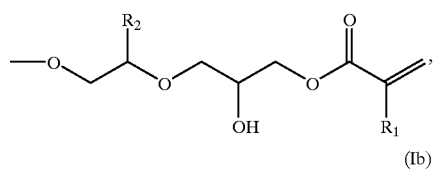

(Ib)

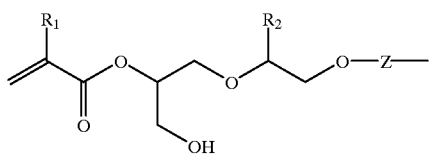

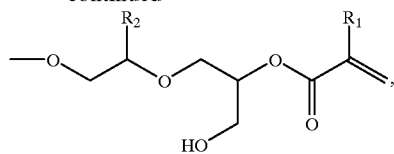

wherein the substituents $R_1$ are each independently of the other hydrogen or methyl, $R_2$ is an unsubstituted $C_1$–$C_{20}$alkyl group or a $C_1$–$C_{20}$alkyl group which is substituted by one or more than one substituent selected from the group consisting of hydroxy, $C_6$–$C_{14}$aryl and halogen, an unsubstituted phenyl group or a phenyl group which is substituted by one or more than one substituent selected from the group consisting of $C_1$–$C_6$alkyl, hydroxy or halogen, or is a radical of formula —$CH_2$—$OR_3$, wherein $R_3$ is an unsubstituted $C_1$–$C_{20}$alkyl group or a $C_1$–$C_{20}$alkyl group which is substituted by one or more than one substituent selected from the group consisting of hydroxy, $C_6$–$C_{14}$aryl and halogen, an unsubstituted phenyl group or a phenyl group which is substituted by one or more than one substituent selected from the group consisting of $C_1$–$C_6$alkyl, hydroxy and halogen, or is a $C_2$–$C_6$alkenyl group, a $C_2$–$C_{20}$acyl group or an unsubstituted cyclohexylcarbonyl group or a cyclohexylcarbonyl group which is substituted by one or more than one substituent selected from the group consisting of $C_1$–$C_6$alkyl, hydroxy and halogen, Z is a group of formulae (IIa)–(IIe)

(IIa)

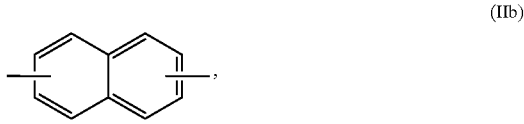

(IIb)

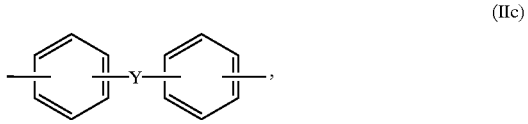

(IIc)

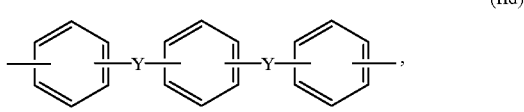

(IId)

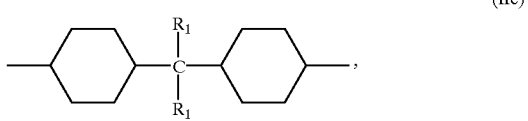

(IIe)

wherein Y is a direct bond, $C_1$–$C_6$alkylene, —S—, —O—, —SO—, —$SO_2$— or —CO—, and $R_1$ is hydrogen or methyl, and wherein the aromatic and cycloaliphatic rings of formulae (IIa)–(IIe) are unsubstituted or substituted by one or more than one substituent selected from the group consisting of $C_1$–$C_6$alkyl, chloro and bromo.

$R_2$ or $R_3$ as $C_1$–$C_{20}$alkyl may be branched or, preferably, straight-chain alkyl. Typical examples of such alkyl groups are methyl, ethyl, n-propyl, isopropyl, n-butyl, sec-butyl, tert-butyl, n-pentyl, neo-pentyl, n-hexyl, octyl, decyl, dodecyl and icosyl.

The alkyl groups may also be substituted by one or more than one substituent selected from the group consisting of hydroxy, $C_6$–$C_{14}$aryl and halogen. Typical examples of substituted alkyl groups are hydroxymethyl, 2-hydroxyethyl, 2-hydroxypropyl, 2-chloropropyl, 2,3-dichlorobutyl, 2-phenylethyl and 2,3-diphenylbutyl.

$R_3$ as $C_2$–$C_6$alkenyl may be branched or, preferably, straight-chain alkenyl. Typical examples of alkenyl groups are vinyl, prop-1-enyl, prop-2-enyl, 2-methylprop-2-enyl, n-but-3-enyl, n-pent-4enyl and n-hex-5-enyl. Alkenyl groups containing two or three carbon atoms are preferred, and vinyl, prop-l-enyl and prop-2-enyl are especially preferred.

Typical examples of $C_2$–$C_{20}$acyl groups are acetyl, propionyl, n-butyryl, isobutyryl, pivaloyl, hexyloyl, octyloyl, tetradecyloyl, hexadecyloyl and octadecyloyl.

$R_3$ as phenyl or cyclohexylcarbonyl may be unsubstituted or substituted by one or more than one substituent selected from the group consisting of $C_1$–$C_6$alkyl, hydroxy and halogen. Typical examples of such groups are tolyl, xylyl, mesityl, 2-hydroxyphenyl, 4hydroxyphenyl, 2-chlorophenyl, 4-chlorophenyl, 3,5-dichlorophenyl, 2,4-dichlorophenyl, 2,6-dimethylcyclohexylcarbonyl, 4hydroxycyclohexylcarbonyl, p-hydroxybenzyl, p-chlorobenzyl and o-ethylbenzyl.

The aromatic and cycloaliphatic rings in formulae (IIa)–(IIe) are preferably unsubstituted.

In the compounds of formulae (Ia) and (Ib) $R_2$ is preferably $C_1$–$C_{20}$alkyl, phenyl, $C_1$–$C_{20}$alkoxymethyl, phenoxymethyl or cyclohexylcarbonyloxymethyl.

Especially preferred compounds of formulae (Ia) and (Ib) are those wherein $R_2$ is n-butyl, phenyl, n-butoxymethyl, phenoxymethyl or cyclohexylcarbonyloxymethyl.

The most preferred meaning of $R_2$ is n-butoxymethyl.

Z in formulae (Ia) and (Ib) is preferably a group of formula (IIc) or (IIe).

Compounds of formulae (Ia) and (Ib) are especially preferred wherein Z is

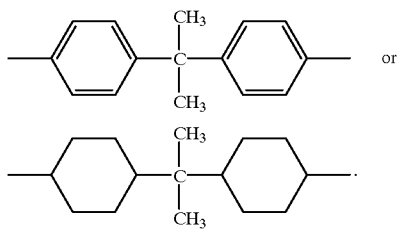

The compounds of formulae (Ia) and (Ib) can be prepared by per se known processes. A further object of the invention is a process for the preparation of compounds of formulae (Ia) and (Ib), which comprises reacting a diglycidyl ether of formula (III)

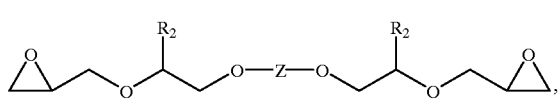

(III)

wherein $R_2$ and Z have the above meanings, in a manner known per se, with acrylic or methacrylic acid.

The diglycidyl compounds of formula (III) are known and disclosed, inter alia, in EP-A 22 073.

The reaction of the diglycidyl compounds of formula (III) with acrylic or methacrylic acid normally gives a mixture of compounds (Ia) and (Ib), compound (Ia) being the main product and compound (Ib) being obtained in comparatively minor amounts (c. 10–20 %). Separation of the two structurally isomeric compounds for use in photosensitive compositions is not necessary.

Illustrative specific examples of the diglycidyl compounds of formula (III) are:
  2,2-bis[p-(3-butoxy-2-glycidyloxypropoxy)phenyl] propane,
  2,2-bis[p-(3-methoxy-2-glycidyloxypropoxy) phenylpropane,
  2,2-bis[p-(3-ethoxy-2-glycidyloxypropoxy)phenyl] propane,
  2,2-bis[p-(3-dodecyloxy-2-glycidyloxypropoxy)phenyl] propane,
  2,2-bis[p-(3-tetradecyloxy-2-glycidyloxypropoxy) phenyl]propane,
  2,2-bis[p-(3-benzyloxy-2-glycidyloxypropoxy)phenyl] propane,
  bis[p-(3-butoxy-2-glycidyloxypropoxy)phenyl]methane,
  1,3-bis[p-(3-phenoxy-2-glycidyloxypropoxy]benzene,
  bis[p-(3-butoxy-2-glycidyloxypropoxy)phenyl]sulfone,
  2,2-bis[p-(3-cyclohexoxy-2-glycidyloxypropoxy)phenyl] propane,
  2,2-bis[4-(3-butoxy-2-glycidyloxypropoxy)-3,5-dibromophenyl]propane,
  2,2-bis[p-(3-allyloxy-2-glycidyloxypropoxy)phenyl] propane,
  2,2-bis[p-(3-phenoxy-2-glycidyloxypropoxy)phenyl] propane,
  2,2-bis[4-(3-butoxy-2-glycidyloxypropoxy)cyclohexyl] propane,
  2,2-bis[p-(3-cyclohexylcarbonyloxy-2-glycidyloxypropoxy)phenyl]propane,
  2,2-bis[p-(2-glycidyloxyhexoxy)phenyl]propane, and
  2,2-bis[p-(2-phenyl-2-glycidyloxyethoxy)phenyl] propane.

A further object of the invention is a photosensitive composition comprising
  (a) 5–65 % by weight of a compound of formula (Ia) or (Ib) according to claim 1,
  (b) 15–70 % by weight of one or more than one bifunctional acrylate or methacrylate having a molecular weight in the range from 150 to 450 and differing from compound of formula (Ia) or (Ib),
  (c) 0–40 % by weight of one or more than one monomeric polyfunctional acrylate or methacrylate having a functionality of not less than 3 and a molecular weight of not more than 600,
  (d) 0–10 % by weight of at least one monofunctional acrylate or methacrylate,
  (e) 0–10 % by weight of N-vinylpyrrolidone or N-vinylcaprolactam,
  (f) 2–10 % by weight of at least one photoinitiator, and
  (g) 0–60 % by weight of at least one urethane acrylate or methacrylate having a functionality of 2–4 and a molecular weight in the range from 500–10 000, such that the sum of the amounts of components (a) to (g) together is 100% by weight Compounds useful as component (b) include the diacrylate and dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis(4-hydroxycyclohexyl)propane, bis(4-hydroxycyclohexyl) methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S.

Such diacrylates and dimethacrylates are known and some are commercially available, typically those sold by the SARTOMER Company under the product names SR 348 for the dimethacrylate of ethoxylated bisphenol A, SR 349 for the diacrylate of ethoxylated bisphenol A, SR 247 for neopentyl glycol diacrylate and SR 344 for polyethylene glycol 400 diacrylate.

It is preferred to use a diacrylate or dimethacrylate of ethoxylated bisphenol A as component (b).

Compounds useful as component (c) are typically triacrylates or trimethacrylates of formula (IV) or (V)

$$R_4\text{—}CH_2\text{—}C\text{(—}CH_2\text{—}R_5)_3 \quad (IV),$$

$$R_5\text{—}CH\text{(—}CH_2\text{—}R_5)_2 \quad (V),$$

wherein $R_4$ is hydrogen, methyl or hydroxyl, and $R_5$ is a radical of formula (VI)

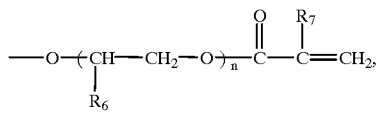

$$\text{—}O\text{—(}CH\text{—}CH_2\text{—}O\text{)}_n\overset{O}{\underset{\|}{C}}\text{—}\underset{R_6}{\overset{R_7}{C}}\text{=}CH_2,\quad (VI)$$

wherein n is 0 or a number from 1–3 and $R_6$ and $R_7$ are each independently of the other hydrogen or methyl.

Among the compounds of formulae (IV) and (V), those compounds of formula (IV) are especially preferred in which $R_4$ is methyl and $R_5$ is a radical of formula (VI), wherein n is 0.

Illustrative examples of compounds which may be used as component (c) are: 1,1,1-trimethylolpropane triacrylate or methacrylate, ethoxylated or propoxylated 1,1,1-trimethylolpropane triacrylate or methacrylate, ethoxylated or propoxylated glycerol triacrylate, pentaerythritol monohydroxy triacrylate or methacrylate; and also higher functional acrylates or methacrylates such as dipentaerythritol monohydroxy pentaacrylate or bis(trimethylolpropane) tetraacrylate. Such compounds are known to the skilled person and some are commercially available.

Preferably the compounds useful as component (c) have a molecular weight in the range from 250 to 700.

It is especially preferred to use trimethylolpropane triacrylate and trimethylolpropane trimethacrylate as component (c).

Component (d) of the novel compositions may be selected from the following compounds: allyl acrylate, allyl methacrylate, methyl (meth)acrylate, ethyl (meth)acrylate, n-propyl (meth)acrylate, n-butyl (meth)acrylate, isobutyl (meth)acrylate, n-hexyl (meth)acrylate, 2-ethylhexyl (meth) acrylate, n-octyl (meth)acrylate, n-decyl (meth)acrylate and n-dodecyl (meth)acrylate, 2-hydroxyethyl (meth)acrylate, 2- and 3-hydroxypropyl (meth)acrylate, 2-methoxyethyl (meth)acrylate, 2-ethoxyethyl (meth)acrylate and 2- or 3-ethoxypropyl (meth)acrylate, tetrahydrofurfurylmethacrylate, 2-(2-ethoxyethoxy) ethylacrylate, cyclohexyl methacrylate, 2-phenoxyethyl acrylate, glycidyl acrylate and isodecyl acrylate. Such products are also known and some are commercially available, as from SARTOMER 2-Phenoxyethylacrylate is especially preferred.

The novel compositions may contain up to 10% by weight of N-vinylpyrrolidone or N-vinylcaprolactam or a mixture thereof as component (e). It is preferred to use N-vinylpyrrolidone.

Any type of photoinitiator which, when irradiated suitably, forms free radicals can be employed as component (f) in the novel compositions. Typical known photoinitiators are benzoins, benzoin ethers, including benzoin, benzoin methyl ether, benzoin ethyl ether and benzoin isopropyl ether, benzoin phenyl ether and benzoin acetate; acetophenones, including acetophenone, 2,2-dimethoxyacetophenone and 1,1-dichloroacetophenone; benzil, benzil ketals such as benzil dimethyl ketal and benzil diethyl ketal; anthraquinones, including 2-methylanthraquinone, 2-ethylanthraquinone, 2-tert-butylanthraquinone, 1-chloroanthraquinone and 2-amylanthraquinone; triphenylphosphine; benzoylphosphine oxides, for example 2,4,6-trimethylbenzoyldiphenylphosphine oxide (Luzirin TPO); benzophenones such as benzophenone and 4,4'-bis(N,N'-dimethylamino)benzophenone; thioxanthones and xanthones; acridine derivatives; phenazine derivatives; quinoxaline derivatives or 1-phenyl-1,2-propanedione; 2–0-benzoyl oxime; 1-aminophenyl ketones or 1-hydroxyphenyl ketones such as 1-hydroxycyclohexyl phenyl ketone, phenyl 1-hydroxyisopropyl ketone and 4-isopropylphenyl 1-hydroxyisopropyl ketone.

Suitable initiators are also are electron transfer initiators of the xanthone type, for example 2,4,5,7-tetraiodo-6hydroxy-9-cyano-3H-xanthen-3-one which, together with suitable electron donors, have a high reactivity in the visible range of the spectrum.

Another class of suitable photoinitiators (f) comprises the ionic dye-counter ion compounds which are capable of absorbing actinic radiation and generating free radicals which initiate the polymerisation of the acrylates (a) to (d) and optionally (g). The compositions of the invention containing ionic dye-counter ion compounds can be cured more variably in this way with visible light within the adjustable wavelength range of 400–700 nm. Ionic dye-counter ion compounds and their mode of action are known, for example from EP-A-0 223 587 and U.S. Pat. Nos. 4,751,102; 4,772,530 and 4,772,541. Typical examples of suitable ionic dye-counter ion compounds are the anionic dye-iodonium ion complexes, the anionic dye-pyrylium ion complexes and, especially, the cationic dye-borate anion compounds of formula

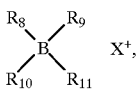

$$\begin{array}{c} R_8 \diagdown \diagup R_9 \\ B \\ R_{10} \diagup \diagdown R_{11} \end{array} \quad X^+,$$

wherein $X^+$ is a cationic dye and $R_8$, $R_9$, $R_{10}$ and $R_{11}$, are each independently of one another an alkyl, aryl, alkaryl, allyl, aralkyl, alkenyl or alkynyl group, or an alicyclic or saturated or unsaturated heterocyclic group.

Particularly suitable photoinitiators which are normally used in conjunction with a HeCd laser as source of irradiation are acetophenones such as 2,2-dialkoxybenzophenones, and α-hydroxyphenylketones, typically 1-hydroxycyclohexylphenyl ketone or (2-hydroxyisopropyl) phenyl ketone (=2-hydroxy-2,2dimethylacetophenone).

A particularly preferred photoinitiator is 1-hydroxycyclohexylphenyl ketone.

The novel compositions may also contain other photoinitiators of different sensitivity to radiation of emission lines of different wavelengths. The inclusion of such photoinitiators effects the better utilisation of a UV/VIS light source which radiates emission lines of different wavelength. It is advantageous to choose these other photoinitiators and to use them in such a concentration that a uniform optical absorption is produced with respect to the emission lines used.

The urethane acrylates used in the novel compositions as component (g) are known to those skilled in the art and can be prepared in known manner, typically by reacting a hydroxyl-terminated polyurethane with acrylic acid or methacrylic acid to the corresponding urethane acrylate, or by reacting an isocyanate-terminated prepolymer with hydroxyalkyl acrylates or methacrylates to the urethane acrylate. Suitable processes are disclosed, inter alia, in EP-A 114 982 and EP-A 133 908. The molecular weight of such acrylates is generally in the range from 400 to 10 000, preferably from 500 to 7000. Urethane acrylates are also commercially available and are sold by UCB under the registered trademark EBECRYL®, by Morton Thiokol under the registered trademark Uvithane® or by the SARTOMER Company under the product names SR 9504, SR 9600, SR 9610, SR 9620, SR 9630, SR 9640 and SR 9650.

It is preferred to use those urethane acrylates with have a molecular weight from 500–7000 and which are prepared preferably from aliphatic educts.

The novel photosensitive compositions can be polymerised by irradiation with actinic light, typically with electron beams, X-rays, UV or VIS light, i.e. with radiation in the wavelength range from 280–650 nm. Particularly suitable light sources are HeCd, argon or nitrogen laser light as well as metal vapour and NdYAG lasers with multiple frequency. Those skilled in the art will know that the appropriate photoinitiator for each selected light source must be chosen and, if necessary, sensitised. It has been found that the depth of penetration of the radiation into the polymerised composition and the processing rate are directly related to the absorption coefficient and the concentration of the photoinitiator. In stereolithography it is preferred to use those photoinitiators which generate the highest number of resulting free radicals and make possible the greatest depth of penentration into the compositions to be polymerised.

The invention further relates to a process for the production of three-dimensional objects from the novel liquid compositions by lithographic methods, especially by stereolithography, in which a layer of novel liquid composition is irradiated over the entire surface or in a predetermined pattern with a UV/VIS light source, such that within the irradiated areas a layer solidifies in a desired layer thickness, then a new layer of novel composition is formed on the solidified layer, which is likewise irradiated over the entire surface or in a predetermined pattern, and such that three-dimensional objects are formed from a plurality of solidified layers which adhere to one another by repeated coating and irradiation.

In this process it is preferred to use a laser light which is preferably computer-controlled.

The novel compositions are distinguished by low viscosity and hence good processing properties. The green models obtained by precuring with laser light and the fully cured objects have good mechanical properties, especially superior flexibility.

The novel compositions can be used typically as adhesive or coating compositions or as formulations for stereolithography or other methods of model construction with photopoplymers.

If the novel compositions are used as coating compositions, clear and hard coats are obtained on wood, paper, metal, ceramic or other surfaces. The coating thickness can vary over a very wide range and be from c. 1 μm to c. 1 mm. Relief images for printed circuit boards or printing plates can be produced from the novel compositions, conveniently by computer-controlled laser light of appropriate wavelength or using a photomask and a suitable light source.

It is preferred to use the novel compositions for the production of photopolymerised layers, especially in the form of three-dimensional objects which are formed from a plurality of solidified layers which adhere to one another.

EXAMPLES

I. Preparation of the Novel Acrylates and Methacrylates

I.1. Acrylate A: Diacrylate of 2,2-bis(p-(3-butoxy-2-glycidyloxypropoxy)phenyl]propane Method I: 100 g of 2,2-bis[p-(3-butoxy-2-glycidyloxypropoxy)phenyl]propane (prepared according to EP-A 22 073) having an epoxy value of 2.9 eq/kg are dissolved in 250 ml of toluene. Then 1 g of tetraethylammonium bromide and 0.2 g of hydroquinone m ether are added and the mixture is heated to 80° C. A mixture of 22.98 g (0.32 mol) of acrylic acid and 0.17 g of hydroquinone monomethyl ether is then slowly added dropwise. The reaction mixture is kept at 80° C. until the epoxy value is less than 0.1 eq/kg (c. 14 h). The reaction mixture is then cooled to room temperature and extracted with a 5% aqueous solution of $NaHCO_3$ and then with water. The organic phase is dried and concentrated first on a rotary evaporator and then under a high vacuum.

Yield: 106.94 g (88.5%).

Method II: 0.2 g of di-tert-butyl p-cresol are added to 343.9 g of 2,2-bis[p-(3-butoxy-2-glycidyloxypropoxy)phenyl]propane (prepared according to EP-A 22 073) having an epoxy value of 2.9 eq/kg, and the mixture is heated to 110° C. With stirring, a mixture of 72.06 g (1 mol) of acrylic acid, 0.56 g of Nuosyn Chromium® 5 % (fatty acid chromium salt in hydrocarbons, Durham Chemicals, GB) and 0.42 g of di-tert-butyl p-cresol is added dropwise. The mixture is kept at 110° C. until the epoxy value is less than 0.1 eq/kg (c. 4 h). A brownish viscous resin having a double bond value of 2.38 eq/kg is obtained (88.5 % of theory).

I.2. Methacrylate B: Dimethacrylate of 2,2-bis[p-(3-butoxy-2-glycidyloxypropoxy)phenyl]propane 343.9 g of 2,2-bis[p-(3-butoxy-2-glycidyloxypropoxy)phenyl]propane (prepared according to EP-A 22 073) having an epoxy value of 2.9 eq/kg are reacted with 86.09 g (1 mol) of methacrylic acid by method II described above. The mixture is stirred at c. 110° C. until the epoxy value is less than 0.1 eq/kg (c. 4 h). A brownish viscous resin having a double bond content of 2.26 eq/kg is obtained (87.2 % of theory).

I.3. Acrylate C: Diacrylate of 2,2-bis[4-(3-butoxy-2-glycidyloxypropoxy)cyclohexyl]propane 100 g of 2,2-bis[4-(3-butoxy-2-glycidyloxypropoxy)cyclohexyl]propane (prepared according to EP-A 22 073) having an epoxy value of 2.48 eq/kg are reacted with 19.67 g (0.273 mol) of acrylic acid by method I described above. The solution is stirred for 4 h at 80° C. The epoxy value is then 0.12 eq/kg. After extraction with a 5% aqueous solution of $NaHCO_3$ and then with water, the organic phase is concentrated under a high vacuum.

Yield: 87.8 g (74.5%); Double bond value: 1.91 eq/kg (71.8% of theory).

I.4. Methacrylate D: Dimethacrylate of 2,2-bis[4-(3-butoxy-2-glycidyloxypropoxy)cyclohexyl]propane 82 g of 2,2-bis[4-(3-butoxy-2-glycidyloxypropoxy)cyclohexyl]propane (prepared according to EP-A 22 073) having an epoxy value of 2.48 eq/kg are reacted with 19.2 g (0.223 mol) of methacrylic acid by method I described above. The solution is stirred for c. 32 h at 80° C. The epoxy value is then 0.17 eq/kg. After extraction with a 5% aqueous solution of NaHCO$_3$ and then with water, the organic phase is concentrated under a high vacuum.

Yield: 84.33 g (84.7%); Double bond value: 1.90 eq/kg (74.5% of theory).

I.5. Acrylate E: Diacrylate of 2,2-bis[p-(3-phenoxy-2-glycidyloxypropoxy)phenyl]propane 50 g of 2,2-bis[p-(3-phenoxy-2-glycidyloxypropoxy)phenyl]propane (prepared according to EP-A 22 073) having an epoxy value of 2.7 eq/kg are reacted with 9.76 g (0.135 mol) acrylic acid by method II described above to give a viscous resin having a double bond value of 2.28 eq/kg (85.8% of theory).

I.6. Acrylate F: Diacrylate of 2,2-bis[p-(3-cyclohexylcarbonyloxy-2-glycidyloxypropoxy)phenyl]propane a) Preparation of 2,2-bis[p-(3-cyclohexylcarbonyloxy-2-glycidyloxypropoxy)phenyl]propane (according to EP-A 22 073):

With stirring, 50 g (0.27 mol) of glycidyl cyclohexanoate, 30 g (0.135 mol) of bisphenol A and 0.8 g of benzyltrimethylammonium bromide are heated to 110° C. When the exothermic reaction has subsided (rise in temperature to 140° C.), the reaction mixture is further stirred at 10° C. until the epoxy value is less than 0.1 eq/kg (2 h).

35 g (0.059 mol) of the resultant reaction product are reacted with 87 g (0.94 mol) of epichlorohydrin and 0.77 g of tetramethylammonium bromide by the method described in EP-A 22 073. After addition of 9.6 g (0.12 mol) of 50% aqueous sodium hydroxide and removal of the water under vacuum, the product is isolated and dried.

Yield: 15.5 g (37%); Epoxy value: 1.90 eq/kg (74.5% of theory).

b) Preparation of the diacrylate:

12.97 g (0.27 mol) of 2,2-bis[p-(3-cyclohexylcarbonyloxy-2-glycidyloxypropoxy)phenyl]propane prepared according to a) are reacted with 1.8 g (0.025 mol) of acrylic acid by method II described above to give a viscous resin having a double bond value of 1.84 eq/kg (78.3% of theory).

I.7. Acrylate G: Diacrylate of 2,2-bis[p-(2-glycidyloxyhexoxy)phenyl]propane a) Preparation of 2,2-bis[p-(2-glycidyloxyhexoxy)phenyl]propane (according to EP-A 22 073):

With stirring, 100.2 g (1 mol) of butyl oxirane, 114 g (0.5 mol) of bisphenol A and 2.14 g of benzyltrimethylammonium bromide are heated to 110° C. When the exothermic reaction has subsided (rise in temperature to 115° C.), the reaction is further stirred at 110° C. until the epoxy value is less than 0.1 eq/kg (16 h).

85.52 g (0.2 mol) of the resultant reaction product are reacted with 296 g (3.2 mol) of epichlorohydrin and 1.32 g of tetramethylammonium bromide according to the method described in EP-A 22 073. After addition of 33.6 g (0.42 mol) of 50% aqueous sodium hydroxide and removal of the water under vacuum, the product is isolated and dried.

Yield: 87.2 g (80.6%); Epoxy value: 2.51 eq/kg (67.9% of theory).

b) Preparation of the Diacrylate:

100 g (0.31 mol) of 2,2-bis[p-(2-glycidyloxyhexoxy)phenyl,p4pane prepared according to a) are reacted with 15.85 g (0.22 mol) of acrylic acid by method II described above to give a viscous resin having a double bond value of 1.87 eq/kg (64% of theory).

I.8. Acrylate H: Diacrylate of 2,2-bis[p-(2-phenyl-2-glycidyloxyethoxy)phenyl]propane a) Preparation of 2,2-bis[p-(2-phenyl-2-glycidyloxyethoxy)phenyl]propane (according to EP-A 22 073):

With stirring, 100 g (0.83 mol) of phenylethylene oxide, 94.7 g (0.415 mol) of bisphenol A and 1.95 g of benzyltrimethylammonium bromide are heated to 110° C. When the exothermic reaction has subsided (rise in temperature to 115° C.), the reaction mixture is further stirred at 110° C. until the epoxy value is less than 0.1 eq/kg (5 h).

80 g (0.17 mol) of the resultant reaction product are reacted with 251.6 g (2.72 mol) of epichlorohydrin and 0.9 g of tetramethylammonium bromide according to the method described in EP-A 22 073. After addition of 28.8 g (0.36 mol) of 50% aqueous sodium hydroxide and removal of the water under vacuum, the product is isolated and dried.

Yield: 60.5 g (58.5%); Epoxy value: 2.56 eq/kg (78% of theory).

b) Preparation of the Diacrylate:

25 g (0.032 mol) of 2,2-bis[p-(2-phenyl-2-glycidyloxyethoxy)phenyl]propane prepared according to a) are reacted with 4.6 g (0.064 mol) of acrylic acid by method II described above to give a viscous resin having a double bond value of 2.12 eq/kg (76.8% of theory).

II. Use Examples

Use of the novel diacrylates and dimethacrylates in formulations for stereolithography.

Example 1

49.85 g of acrylate A, 26 g of the dimethacrylate of ethoxylated bisphenol A (SR 348, Sartomer), 14 g of trimethylolpropane trimethacrylate (SR 350, Sartomer) and 6 g of phenoxyethyl acrylate (SR 339, Sartomer) are mixed at c. 60° C. with 0.15 g of hydroquinone monomethyl ether and 4 g of 1-hydroxycyclohexyl phenyl ketone. The resultant homogeneous liquid formulation has a viscosity of 631 mPa·s at 30° C. A moulded article (green mode cured from this formulation using a He/Cd laser (40 mJ/cm$^2$) has a modulus of elasticity (DIN 53 371; green strength) of 16.2 N/mm$^2$, a tensile strength $\sigma_{max}$ (DIN 53 455) of 1.31 N/mm$^2$ and a flexural elongation ε (DIN 53 455) of 10.2%.

The green model is fully cured by irradiation for 30 minutes with UV/VIS light The moulded article then has the following properties:

modulus of elasticity: 1610 N/mm$^2$ tensile strength $\sigma_{max}$: 32.8 N/mm$^2$ flexural elongation ε: 7.2%

Examples 2–10

Formulations of the components listed in Tables 1 and 2 are prepared and processed to three-dimensional objects as described in Example 1. The properties of the liquid formulations, of the green models and of the fully cured moulded articles are indicated in Table 2.

TABLE 1

| Example | 1 | 2 | 3 | 4 |
|---|---|---|---|---|
| actylate A [g] | 49.85 | | 36.85 | |
| methacrylate B [g] | | 49.85 | | |
| methacrylate D [g] | | | | 48.85 |
| dimethacrylate of ethoxylated bisphenol A [g] (SR 348, Sartomer) | 26.0 | 26.0 | 6.0 | |
| diacrylate of ethoxylated bisphenol A [g] (SR 349, Sartomer) | | | 26.0 | 25.0 |
| trimethylolpropane trimethacrylate (SR 350, Sartomer) [g] | 14.0 | 14.0 | 6.0 | |
| trimethylolpropane triacrylate (SR 351, Sartomer) [g] | | | 14.0 | 12.0 |
| phenoxyethyl acrylate (SR 339, Sartomer) [g] | 6.0 | 6.0 | 6.0 | 5.0 |
| 1-hydroxycyclohexyl phenyl ketone [g] | 4.0 | 4.0 | 5.0 | 4.0 |
| N-vinylpyrrolidone [g] | | | | 5.0 |
| hydroquinone monomethyl ether [g] | 0.15 | 0.15 | 0.15 | 0.15 |
| Viscosity η of the liquid formulation at 30° C. [mPa · s] | 631 | 578 | 451 | 302 |
| Properties of the green models | | | | |
| modulus of elasticity [N/mm²] | 16.2 | 20.4 | 35.8 | |
| tensile strength σ$_{max}$ [N/mm²] | 1.31 | 1.56 | 2.70 | |
| flexural elongation ε [%] | 10.2 | 20.4 | 12.5 | |
| Properties of the fully cured moulded articles | | | | |
| modulus of elasticity [N/mm²] | 1610 | 1734 | 1660 | 251.3 |
| tensile strength σ$_{max}$ [N/mm²] | 32.8 | 35.0 | 32.0 | 9.8 |
| flexural elongation ε [%] | 7.2 | 4.1 | 5.0 | 11.0 |

TABLE 2

| Example | 5 | 6 | 7 | 8 | 9 | 10 |
|---|---|---|---|---|---|---|
| acrylate A [g] | 9.0 | | 30.0 | | 19.0 | |
| methacrylate B [g] | | 9.0 | | 30.0 | | 19.0 |
| dimethacrylate of ethoxylated bisphenol A (SR 348, Sartomer) [g] | 29.0 | 29.0 | 5.0 | 5.0 | 29.0 | 29.0 |
| diacrylate of ethoxylated bisphenol A (SR 349, Sartomer) | | | 20.0 | 20.0 | | |
| polyethylene glycol 400 diacrylate [g] (SR 344, Sartomer) | 14.0 | 14.0 | | | 14.0 | 14.0 |
| neopentylglycol diacrylate | 7.0 | 7.0 | | | 7.0 | 7.0 |
| trimethylolpropane triacrylate [g] (SR 351, Sartomer) | | | 12.0 | 12.0 | | |
| phenoxyethyl acrylate [g] | 1.0 | 1.0 | 5.0 | 5.0 | 1.0 | 1.0 |
| 1-hydroxycyclohexyl phenyl ketone [g] | 5.0 | 5.0 | 5.0 | 5.0 | 5.0 | 5.0 |
| aliphatic urethane acrylate [g] (SR 9640, Sartomer, MG: 1300, viscosity at 60° C.: 18000 mPa · s) | 35.0 | 35.0 | 23.0 | 23.0 | 25.0 | 25.0 |
| viscosity η of the liquid formulation at 30° C. [mPa · s] | 1490 | 1600 | 2250 | 2120 | 1010 | 925 |
| Properties of the green models | | | | | | |
| modulus of elasticity [N/mm²] | 23.9 | 59.4 | 52.2 | 36.4 | 19.6 | 27.3 |
| tensile strength σ$_{max}$ [N/mm²] | 3.7 | 3.8 | 3.7 | 3.9 | 2.9 | 3.3 |
| flexural elongation ε [%] | 22.8 | 17.4 | 13.6 | 20.0 | 19.9 | 18.8 |
| Properties of the fully curred moulded articles | | | | | | |
| modulus of elasticity [N/mm²] | 729 | 948 | 772 | 1340 | 941 | 1102 |
| tensile strength σ$_{max}$ [N/mm²] | 26.6 | 27.8 | 18.7 | 24.8 | 25.8 | 30.0 |
| flexural elongation ε [%] | 21.0 | 17.4 | 7.5 | 6.3 | 13.5 | 16.0 |

What is claimed is:

1. A compound of formula (Ia) or (Ib)

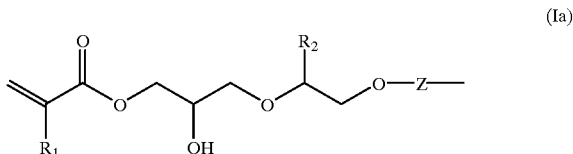

(Ia)

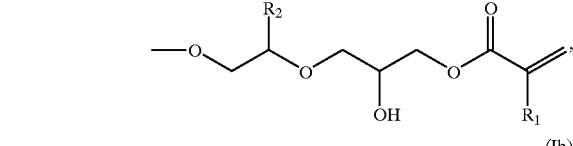

(Ib)

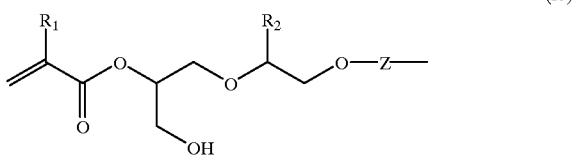

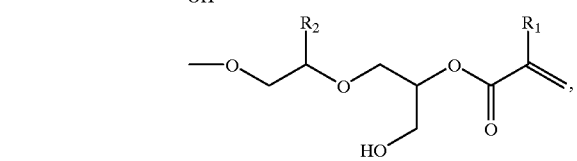

wherein the substituents $R_1$ are each independently of the other hydrogen or methyl, $R_2$ is an unsubstituted $C_1$–$C_{20}$alkyl group or a $C_1$–$C_{20}$alkyl group which is substituted by one or more than one substituent selected from the group consisting of hydroxy, $C_6$–$C_{14}$aryl and halogen, an unsubstituted phenyl group or a phenyl group which is substituted by one or more than one substituent selected from the group consisting of $C_1$–$C_6$alkyl, hydroxy or halogen, or is a radical of formula—$CH_2$—$OR_3$, wherein $R_3$ is an unsubstituted $C_1$–$C_{20}$alkyl group or a $C_1$–$C_{20}$alkyl group which is substituted by one or more than one substituent selected from the group consisting of hydroxy, $C_6$–$C_{14}$aryl and halogen, an unsubstituted phenyl group or a phenyl group which is substituted by one or more than one substituent selected from the group consisting of $C_1$–$C_6$alkyl, hydroxy and halogen, or is a $C_2$–$C_6$alkenyl group, a $C_2$–$C_{20}$acyl group or an unsubstituted cyclohexylcarbonyl group or a cyclohexylcarbonyl group which is substituted by one or more than one substituent selected from the group consisting of $C_1$–$C_6$alkyl, hydroxy and halogen, Z is a group of formulae (IIa)–(IIe)

(IIa)

(IIb)

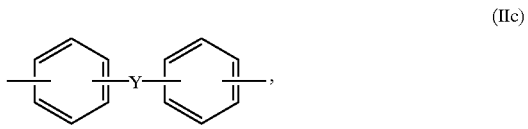

(IIc)

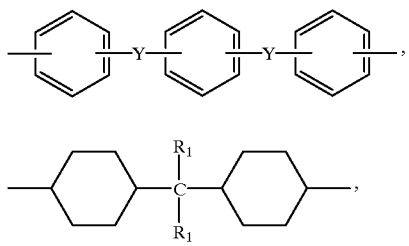
(IId)

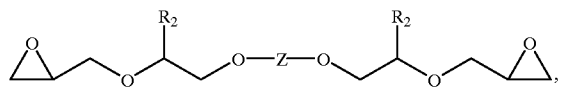
(IIe)

wherein Y is a direct bond, $C_1$–$C_6$alkylene, —S—, —O—, —SO—, —SO$_2$— or —CO—, and $R_1$ is hydrogen or methyl, and wherein the aromatic and cycloaliphatic rings of formulae (IIa)–(IIe) are unsubstituted or substituted by one or more than one substituent selected from the group consisting of $C_1$–$C_6$alkyl, chloro and bromo.

2. A compound of formula (Ia) or (Ib) according to claim 1, wherein $R_2$ is preferably $C_1$–$C_{20}$alkyl, phenyl, $C_1$–$C_{20}$alkoxymethyl, phenoxymethyl or cyclohexylcarbonyloxymethyl.

3. A compound of formula (Ia) or (Ib) according to claim 1, wherein $R_2$ is n-butyl, phenyl, n-butoxymethyl, phenoxymethyl or cyclohexylcarbonyloxymethyl.

4. A compound of formula (Ia) or (Ib) according to claim 1, wherein $R_2$ is n-butoxymethyl.

5. A compound of formula (Ia) or (Ib) according to claim 1, wherein Z is a group of formula (IIc) or (IIe).

6. A compound of formula (Ia) or (Ib) according to claim 1, wherein Z is

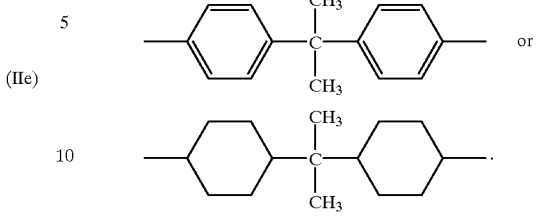

7. A process for the preparation of a compound of formula (Ia) or (Ib) according to claim 1, which comprises reacting a diglycidyl ether of formula (III)

(III)

wherein $R_2$ and Z are as defined in claim 1, with acrylic or methacrylic acid.

* * * * *